(12) United States Patent
Ozawa

(10) Patent No.: US 9,289,113 B2
(45) Date of Patent: *Mar. 22, 2016

(54) PROCESSOR FOR ELECTRONIC ENDOSCOPE AND ELECTRONIC ENDOSCOPE APPARATUS

(75) Inventor: Ryo Ozawa, Saitama (JP)

(73) Assignee: HOYA CORPORATION, Tokyo (JP)

( * ) Notice: Subject to any disclaimer, the term of this patent is extended or adjusted under 35 U.S.C. 154(b) by 226 days.

This patent is subject to a terminal disclaimer.

(21) Appl. No.: 13/823,996

(22) PCT Filed: Aug. 25, 2011

(86) PCT No.: PCT/JP2011/069135
§ 371 (c)(1),
(2), (4) Date: Mar. 15, 2013

(87) PCT Pub. No.: WO2012/056802
PCT Pub. Date: May 3, 2012

(65) Prior Publication Data
US 2013/0169774 A1   Jul. 4, 2013

(30) Foreign Application Priority Data

Oct. 26, 2010   (JP) .................................. 2010-239205

(51) Int. Cl.
*H04N 7/18*   (2006.01)
*A61B 1/05*   (2006.01)
(Continued)

(52) U.S. Cl.
CPC .............. *A61B 1/05* (2013.01); *A61B 1/00009* (2013.01); *G02B 23/2484* (2013.01); *H04N 1/2166* (2013.01); *H04N 7/183* (2013.01); *H04N 2201/0079* (2013.01)

(58) Field of Classification Search
CPC ....................................................... A61B 1/05

USPC .......................................................... 348/65
See application file for complete search history.

(56) References Cited

U.S. PATENT DOCUMENTS 4,901,143 A    2/1990 Uehara et al.
5,270,810 A *  12/1993 Nishimura ...................... 348/65
(Continued)

FOREIGN PATENT DOCUMENTS

CN    101005795    7/2007
CN    101040774    9/2007
(Continued)

OTHER PUBLICATIONS

China Office action, dated Dec. 3, 2014 along with an English translation thereof.
(Continued)

*Primary Examiner* — Dave Czekaj
*Assistant Examiner* — Alison Slater
(74) *Attorney, Agent, or Firm* — Greenblum & Bernstein, P.L.C.

(57) ABSTRACT

A processor for an electronic endoscope includes first and second image storing units; a motion detector obtains a difference of image data; and a controller executes control in one of a first mode where the image data is sequentially converted into the video signal, and the image data and the difference are sequentially stored in the first and second image storing units; a second mode where the image data stored in the first image storing unit is outputted, and the generated image data and the difference are sequentially stored in the second image storing unit; and a third mode where the image data stored in the second image storing unit is outputted, and the generated image data and the difference are sequentially stored in the first image storing unit, and in the second and the third modes, based on the difference.

11 Claims, 7 Drawing Sheets

(51) Int. Cl.
*A61B 1/00* (2006.01)
*G02B 23/24* (2006.01)
*H04N 1/21* (2006.01)

(56) References Cited

U.S. PATENT DOCUMENTS

| | | | |
|---|---|---|---|
| RE34,504 E | | 1/1994 | Uehara et al. |
| 5,617,136 A | | 4/1997 | Iso et al. |
| 6,489,987 B1 | | 12/2002 | Higuchi et al. |
| 2007/0223797 A1 | | 9/2007 | Kaneko |
| 2008/0303898 A1 | * | 12/2008 | Nishimura .................... 348/65 |
| 2009/0040235 A1 | | 2/2009 | Matsuda |
| 2009/0135249 A1 | | 5/2009 | Hirakawa |
| 2011/0122068 A1 | * | 5/2011 | Venon ......................... 345/169 |
| 2013/0123576 A1 | | 5/2013 | Ozawa |

FOREIGN PATENT DOCUMENTS

| | | | | |
|---|---|---|---|---|
| CN | 101778591 | | 7/2010 | |
| JP | 63-214231 | | 9/1988 | |
| JP | 1-279689 | | 11/1989 | |
| JP | 4-33651 | | 2/1992 | |
| JP | 4-71546 | | 3/1992 | |
| JP | 7-289507 | | 11/1995 | |
| JP | 10-323326 | | 12/1998 | |
| JP | 11-197104 | | 7/1999 | |
| JP | 11-216107 | | 8/1999 | |
| JP | 2002-65667 | | 3/2002 | |
| JP | 3497231 | | 2/2004 | |
| JP | 2007-301398 | | 11/2007 | |
| JP | 2008-302146 | | 12/2008 | |
| WO | WO 2007077554 A2 | * | 7/2007 | ............... H04N 1/46 |
| WO | WO 2010086751 A2 | * | 8/2010 | ............... G06T 5/00 |

OTHER PUBLICATIONS

China Office action in China Patent Application No. 201180048320.9, dated Nov. 17, 2014 along with an English translation thereof.
Japan Office action in Japan Patent Application No. 2010-226806, dated Jun. 2, 2014 along with an English translation thereof.
Office Action in U.S. Appl. No. 13/813,231, mail date is Oct. 14, 2015.

* cited by examiner

PROCESSOR FOR ELECTRONIC ENDOSCOPE AND ELECTRONIC ENDOSCOPE APPARATUS

TECHNICAL FIELD

The present invention relates a processor for an electronic endoscope which processes an image signal from an electronic endoscope and displays video, for example, on a monitor, and an electronic endoscope apparatus including the above described electronic endoscope and the processor.

BACKGROUND ART

Electronic endoscope apparatuses have been widely used for observation and diagnosis for a body cavity. The electronic endoscope apparatus includes an image pick-up device at its tip portion, and includes an electronic endoscope which outputs an image signal of an image shot by the image pick-up device, and a processor for the electronic endoscope which converts the image signal into a video signal having a predetermined format (e.g., a video signal in NTSC format) and displays the video, for example, on a monitor.

The processor for the electronic endoscope displays the image picked up by the electronic endoscope on the monitor as a moving image. Further, the processor for the electronic endoscope has the function of displaying the picked up image as a still image in order to make it possible to more specifically observe an observation target portion.

Displaying of the still image is triggered, for example, upon detection of pressing of an operation button provided on the electronic endoscope or the processor for the electronic endoscope. That is, a frame displayed on a monitor when the operation button is pressed or a next frame is continued to be displayed as a still image.

In the above described configuration, a user of the electronic endoscope is required to press the operation button at an appropriate timing while checking the moving image displayed on the monitor. However, since it is necessary to operate the electronic endoscope and press the operation button while checking the monitor, it is not easy to obtain a desired still image due to delay of the pressing timing of the operation button. For example, when the operation button is pressed while the observation target portion is moving, a problem arises that a blurry still image or a still image affected by color drift is obtained.

In order to prevent occurrence of a blurry image or a still image affected by color drift, a processor for an electronic endoscope having the function described in Japanese Patent Publication No. JP3497231B (hereafter, referred to as patent document 1) has been proposed. The processor for the electronic endoscope described in patent document 1 is configured to store image data of a plurality of latest frames in a memory, and when an operation for obtaining a still image (e.g., pressing of an operation button) is performed, the processor selects an image having a lower level of blur or color drift and displayed the selected image as a still image.

SUMMARY OF THE INVENTION

Through use of the processor for the electronic endoscope described in patent document 1, a still image having a lower level of blur or color drift can be obtained. However, regarding the configuration described in patent document 1, it is impossible to recognize how long ago the image being displayed as a still image was shot. Therefore, if a diseased portion has largely moved in the screen, the difference between the moving image being displayed and the obtained still image becomes large. In this case, a problem arises that it takes more time to recognize the diseased portion. In addition, if a still image having a lower level of blur or color drift is not a desired image, it becomes necessary to re-shoot a still image. However, in the configuration described in patent document 1, no image data is stored in a memory during a time period from a time when an operation for obtaining a still image is conducted to a time when the still image is displayed on the monitor. Therefore, if re-shooting of a still image is required, it becomes necessary to wait until image data is stored again in the memory.

The present invention is made to solve the above described problem. That is, the objection of the invention is to provide a processor for an electronic endoscope and an electronic endoscope apparatus capable of easily recognize a diseased portion even when a difference between a moving image being displayed on a monitor and an obtained still image is large, and capable of reliably obtaining a desired still image within a relatively short time period.

To achieve the above described object, according to the invention, there is provided a processor for an electronic endoscope for processing an image signal from the electronic endoscope and displaying an image on a monitor, comprising: an image data generating means which generates image data from the image signal; first and second image storing means each of which is capable of storing a plurality of frames of image data; a motion detection means which obtains a difference for each of the image data by comparing the image data with the image data of one frame ago; a signal processing means which converts the image data into a video signal which can be displayed on the monitor; and a control means which controls the signal processing means and the first and second image storing means. The control means executes control in one of: a first mode in which the image data generated by the image data generating means is sequentially converted into the video signal and is outputted, and the image data and the difference are sequentially stored in the first and second image storing means; a second mode in which the image data stored in the first image storing means is converted into the video signal and is outputted, and the image data generated by the image data generating means and the difference are sequentially stored in the second image storing means; and a third mode in which the image data stored in the second image storing means is converted into the video signal and is outputted, and the image data generated by the image data generating means and the difference are sequentially stored in the first image storing means. In the second and the third modes, the difference is monitored, and, based on the difference, a first reproduction mode in which a plurality of image data stored in the first image storing means or the second image storing means is successively converted into the video signal in reverse chronological order in regard to stored times is switched to a second reproduction mode in which one of the plurality of image data stored in the first and the second image storing means is repeatedly converted into the video signal and is outputted.

With this configuration, for observation of an image shot by the electronic endoscope as a moving image, control is executed in the first mode. For obtaining a still image, the mode is switched to the second mode or the third mode so that a plurality of latest image data stored in the first and second image storing means is successively displayed in a rewinding manner. Then, based on the difference, appropriate image data having a lower level of blur and color drift is automatically obtained and displayed on the monitor. In the above described configuration, image data of an image shot by the electronic endoscope is stored in both of the first image storing means and the second image storing means. Therefore, even if an operator needs to additional obtain a different still image after the operator has displayed a still image in the second mode, the operator is able to obtain a still image in the third mode without waiting for accumulation of new image data, because the latest image data including images shot by the electronic endoscope in the second mode is stored in the second image storing means.

The control means may compare the difference with a predetermined threshold, and when the difference becomes smaller than or equal to the predetermined threshold, the control means may switch from the first reproduction mode to the second reproduction mode.

In the first reproduction mode, the plurality of image data stored in the first and the second image storing means is converted into the video signal at intervals of a few frames and is outputted. Since, in this configuration, thinning out of frames is performed in the first reproduction mode when the mode is switched from the first mode to the second and the third modes, it becomes possible to automatically obtain a still image more rapidly.

The processor may further comprise a judgment means which receives an input of a control signal for switching from the first mode to the second or the third mode and makes a judgment on which of the second mode and the third mode the control means switches to when the control signal is inputted, and the control means may switch from the first mode to the second or the third mode based on a judgment result of the judgment means.

In this case, the judgment means may make a judgment such that the second mode and the third mode are alternately switched each time the control signal is inputted.

The judgment means may make a judgment to switch from the first mode to the third mode only when the control signal is inputted within a predetermined time from a time when switching from the second mode to the first mode is performed. In this case, the predetermined time corresponds to a number of pieces of image data which can be stored in the first image storing means.

According to another aspect, according to the invention, there is provided a processor for an electronic endoscope for processing an image signal from the electronic endoscope and displaying an image on a monitor, comprising: an image data generating means which generates image data from the image signal; first and second image storing means each of which is capable of storing a plurality of frames of image data; a motion detection means which, when the image data stored in the first and second image storing means is outputted, obtains a difference by comparing the image data with the image data outputted one frame ago; a signal processing means which converts the image data into a video signal which can be displayed on the monitor; and a control means which controls the signal processing means and the first and second image storing means. The control means executes control in one of: a first mode in which the image data generated by the image data generating means is sequentially converted into the video signal and is outputted, and the image data is sequentially stored in the first and second image storing means; a second mode in which the image data stored in the first image storing means is converted into the video signal and is outputted, and the image data generated by the image data generating means is sequentially stored in the second image storing means; and a third mode in which the image data stored in the second image storing means is converted into the video signal and is outputted, and the image data generated by the image data generating means is sequentially stored in the first image storing means. In the second and the third modes, the difference is monitored, and, based on the difference, a first reproduction mode in which a plurality of image data stored in the first image storing means or the second image storing mean is successively converted into the video signal in reverse chronological order in regard to stored times is switched to a second reproduction mode in which one of the plurality of image data stored in the first and the second image storing means is repeatedly converted into the video signal and is outputted.

With this configuration, the difference is obtained when the image data stored in the first and second image storing means is outputted. Therefore, there is no need to separately store the difference.

According to the invention, an electronic endoscope apparatus may comprise: one of the above described processors for an electronic endoscope; and an electronic endoscope connected to the processor for the electronic endoscope. The electronic endoscope comprises: a first input means that accepts an input for designating switching from the first mode to the second or the third mode; and a second input means that accepts an input for designating switching from the second and the third modes to the first mode.

With this configuration, it becomes possible to obtain a still image and to release displaying of a still image by providing inputs through the first input means and the second input means.

The first input means may be identical with the second input means.

As described above, according to the invention, a processor for an electronic endoscope and an electronic endoscope apparatus capable of easily recognize a diseased portion even when a difference between a moving image being displayed on a monitor and an obtained still image is large, and capable of reliably obtaining a desired still image within a relatively short time period are provided.

EMBODIMENTS FOR CARRYING OUT THE INVENTION

In the following, embodiments of the present invention are explained in detail with reference to the accompanying drawings.

(First Embodiment)

Figure 1:
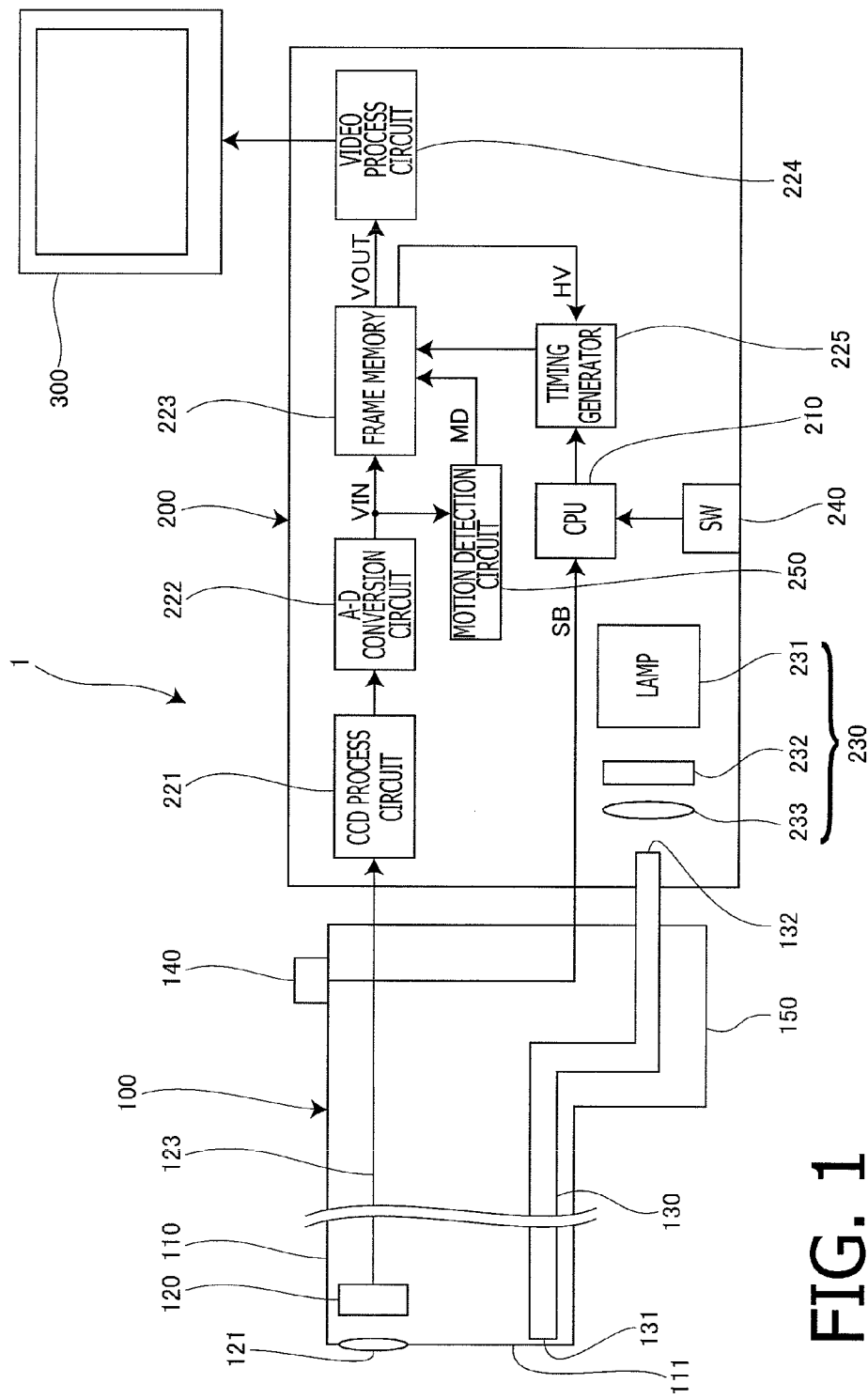
FIG. 1 is a block diagram of a electronic endoscope apparatus according to a first embodiment of the invention.

An electronic endoscope apparatus 1 according to a first embodiment of the invention is explained with reference to FIGS. 1 to 4. FIG. 1 is a block diagram of the electronic endoscope apparatus 1 according to the first embodiment of the invention. The electronic endoscope apparatus 1 according to the embodiment includes an electronic endoscope 100, a processor 200 for the electronic endoscope, and a monitor 300.

An objective lens 121 and an image pick-up device 120 are accommodated at a tip portion (an insertion tube tip part) 111 in an insertion tube 110 of the electronic endoscope 100. The objective lens 121 converges a subject image near to the insertion tube tip part 111 onto a light receiving surface of the image pick-up device 120.

The image pick-up device 120 outputs an image signal corresponding to the image converged onto the light receiving surface. The image signal is transmitted to a CCD process circuit 221 of the processor 200 for the electronic endoscope via a signal cable 123 inserted into the inside of the insertion tube 110. The image pick-up device 120 is controlled by timing pulses inputted to the image pick-up device 120 from a CCD driving circuit (not shown) accommodated in a connector portion 150 of the electronic endoscope 100. Output timing of the timing pulses by the CCD driving circuit is controlled by a microcomputer (not shown) accommodated in the connector portion 150. In FIG. 1, the electronic endoscope 100 and the processor 200 for the electronic endoscope are illustrated apart from each other for convenience of explanation; however, when the electronic endoscope 100 is used, the electronic endoscope 100 is connected to the processor 200 for the electronic endoscope electrically and optically by the connector portion 150.

In the processor 200 for the electronic endoscope, the CCD process circuit 221, an A-D conversion circuit 222, a frame memory 223, a video process circuit 224, a timing generator 225, a CPU 210, a switch 240, an illumination device 230 and a motion detection circuit 250 are accommodated. The CCD process circuit 221 executes processes, such as a noise cut process and an amplifying process, for the image signal inputted from the image pick-up device 120, and transmits the signal to the A-D conversion circuit 222. The A-D conversion circuit 222 converts the analog image signal received from the CCD process circuit 221 into digital image data, and outputs the image data to the frame memory 223 and the motion detection circuit 250. The motion detection circuit 250 detects a moving amount MD of the subject included in the image data based on the image data of each frame outputted from the A-D conversion circuit 222 and the image data of an immediately previous frame, and outputs the moving amount MD to the frame memory 223 (the details will be described later). The frame memory 223 is constituted by a memory capable of storing a plurality of frames of image data and the moving amount MD of the subject outputted from the motion detection circuit 250 (as described later). The frame memory 223 stores the image data and the moving amount MD of the subject under control of the timing generator 225, and outputs the stored image data to the video process circuit 224. The moving amount MD of the subject stored in the frame memory 223 is outputted to the timing generator 225 in synchronization with the image data, under control of the timing generator 225. The video process circuit 224 converts the image data outputted from the frame memory 223 into a video signal (e.g., an NTSC signal) in a predetermined format, and outputs the video signal to the monitor 300 connected to the processor 200 for the electronic endoscope. Through the above described processes, the image near the insertion tube tip part 111 of the electronic endoscope 100 is displayed on the monitor 300.

The CPU 210 of the processor 200 for the electronic endoscope is connected to each component of the processor 200 for the electronic endoscope, such as the switch 240 and the timing generator 255, and totally controls the processor 200 for the electronic endoscope and the electronic endoscope 100 in accordance with programs stored in a memory (not shown). The switch 240 is a user interface through which a user makes settings or inputs instructions to the processor 200 for the electronic endoscope. For example, the switch 240 is a freeze button for obtaining a still image. The CPU 210 makes settings or changes the settings of the processor 200 for the electronic endoscope and the electronic endoscope 100, in accordance with inputs from the switch 240. In this embodiment, when the electronic endoscope 100 is connected to the processor 200 for the electronic endoscope, a scope button 140 of the electronic endoscope 100 is connected to the CPU 210, and the CPU 210 is configured to be able to monitor the state of the scope button 140. That is, when the scope button 140 is pressed, a scope button input signal SB indicative of pressing of the scope button 140 is transmitted to the CPU 210, and the CPU 210 is able to judge whether the scope button 140 of the electronic endoscope 100 is pressed.

The processor 200 for the electronic endoscope includes the illumination device 230 which generates illumination light for illuminating the portion near the insertion tube tip part 111 of the electronic endoscope 100. In the following, explanation is given for the function of the processor 200 for the electronic endoscope as an illumination device.

As shown in FIG. 1, the processor 200 for the electronic endoscope includes a lamp 231, a diaphragm 232 and a condenser lens 233. A light guide 130 is provided to extend from the insertion tube 110 to the connector portion 150 of the electronic endoscope 100. A tip 131 of the light guide 130 is arranged near the insertion tube tip part 111 of the electronic endoscope 100, and a light distribution lens (not shown) is arranged near the insertion tube tip part 111.

The lamp 231 accommodated in the processor 200 for the electronic endoscope produces illumination light through supply of power from a lamp power supply circuit (not shown). The produced illumination light is incident on the condenser lens 233 through the diaphragm 232. The light guide 130 is provided to protrude from the connector portion 150, and in the state where the electronic endoscope 100 is connected to the processor 200 for the electronic endoscope, the light guide 130 is inserted into the inside of the processor 200 for the electronic endoscope. In the state where the light guide 130 is inserted into the processor 200 for the electronic endoscope, a proximal end 132 of the light guide 130 is located at a position on which the illumination light collected by the condenser lens 233 is incident. As a result, the illumination light produced by the lamp 231 is incident on the proximal end 132 of the light guide 130, reaches the tip portion 131 through the light guide 130, and illuminates, through the light distribution lens, a living body tissue near the insertion tube tip part 111. The diaphragm 232 is controlled by the CPU 210. That is, by controlling the diaphragm 232, the CPU 210 adjusts the amount of illumination light incident on the proximal end 132 of the light guide 130 from the lamp 231, and alters the intensity of the illumination light.

Figure 2:
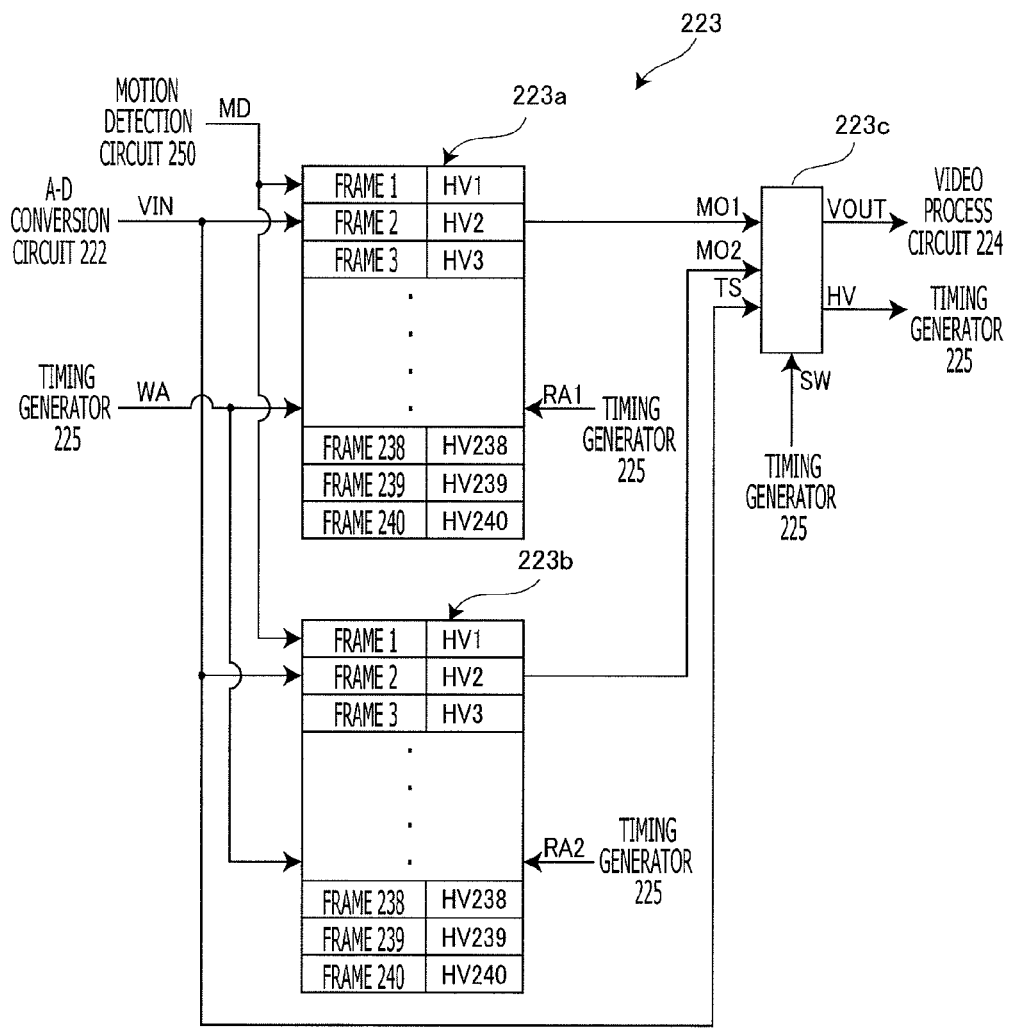
FIG. 2 is a block diagram illustrating a configuration of a frame memory accommodated in a processor for an electronic endoscope according to the first embodiment of the invention.

FIG. 2 is a block diagram illustrating a configuration of the frame memory 223 accommodated in the processor 200 of the electronic endoscope according to the embodiment.

As shown in FIG. 2, the frame memory 233 includes a first memory 223a, a second memory 223b and a switch circuit 223c. Each of the first memory 223a and the second memory 223b is constituted, for example, by a ring-type memory constituted by a DRAM, and the digital image data outputted from the A-D conversion circuit 222 is inputted as input image data VIN, and is sequentially stored at predetermined addresses, e.g., in order of frame 1, frame 2 . . . . To the first memory 223a and the second memory 223b, the moving amount MD of the subject outputted from the motion detection circuit 250 is inputted in synchronization with the input image data VIN, and the moving amount MD of the input image data VIN is sequentially stored together with the input image data VIN at predetermined addresses, for example, in order of HV1 (the moving amount MD of the frame 1), HV2 (the moving amount MD of the frame 2) . . . . Each of the first memory 223a and the second memory 223b according to the embodiment is configured to be able to store 240 frames of image data and the moving amount MD. Furthermore, the first memory 223a and the second memory 223b are connected to the timing generator 225. To the first memory 223a, the writing address WA and a first memory read address RA1 are inputted. To the second memory 223b, the writing address WA and a second memory read address RA2 are inputted.

The writing address WA is data representing an address on each of the first memory 223a and the second memory 223b for storing the input image data VIN and the moving amount MD. In this embodiment, the wiring address WA is inputted in common to the first memory 223a and the second memory 223b. Each of the first memory 223a and the second memory 223b stores the input image data VIN and the moving amount MD at the address indicated by the writing address MD when each of the first memory 223a and the second memory 223b is set in the writable state (the read-inhibited state) by the timing generator 225. The input image data VIN and the moving amount MD stored in the first memory 223a and the second memory 223b can be read by designating the first memory read address RA1 and the second memory read address RA2. When the first memory 223a and the second memory 223b are not set in the read-inhibited state (the writable state) by the timing generator 225, the first memory 223a and the second memory 223b read the input image data VIN and the moving amount MD stored at the addresses indicated by the first memory read address RA1 and the second memory read address RA2, and output the data as a first memory output MO1 and a second memory output MO2, respectively.

The switch circuit 223c is a circuit for performing switching of input signals, and is constituted, for example, with a multiplexer. To the switch circuit 223c, the first memory output MO1, the second memory output MO2 and a through image signal TS (i.e., the input image data VIN) are inputted, and under control of the timing generator 225, one of the first memory output MO1, the second memory output MO2 and the through image signal TS is selected and is outputted as an output image data VOUT. The switch circuit 223c also has the function of separating the image data included in the first memory output MO1 and the second memory output MO2 from the moving amount MD included in the first memory output MO1 and the second memory output MO2. The image data is outputted as the output image data VOUT, and the moving amount MD is outputted as a histogram value HV which is described later. Then, the output image data VOUT outputted from the switch circuit 223c is transmitted to the video process circuit 224, and the histogram value HV is transmitted to the timing generator 225.

Figure 3:
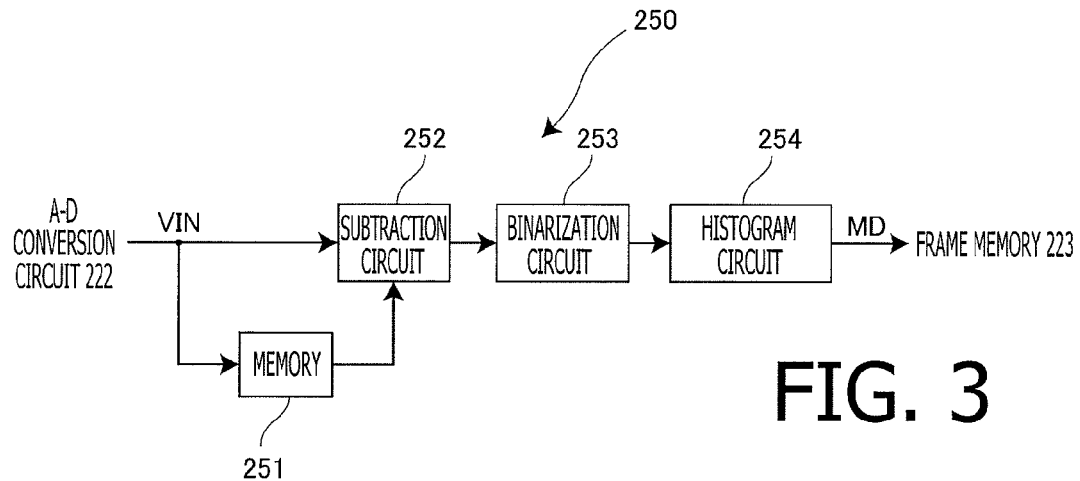
FIG. 3 is a block diagram illustrating a configuration of a motion detection circuit accommodated in a processor for an electronic endoscope according to the first embodiment of the invention.

FIG. 3 is a block diagram illustrating a configuration of the motion detection circuit 250 accommodated in the processor 200 for the electronic endoscope according to the embodiment.

As shown in FIG. 3, the motion detection circuit 250 includes a memory 251 which records a frame of input image data VIN inputted to the motion detection circuit 250 from the A-D conversion circuit 222, a subtraction circuit 252 which obtains a difference between the input image data VIN inputted to the motion detection circuit 250 and the input image data VIN stored in the memory 251 one frame ago, a binarization circuit 253 which binarizes the difference obtained by the subtraction circuit 252 by comparing the difference with a predetermined threshold, and a histogram circuit 254 which obtains a histogram for a binarization result by the binarization circuit 253.

The input image data VIN inputted from the A-D conversion circuit 222 to the motion detection circuit 250 is transmitted to the memory 251 and the subtraction circuit 252. The memory 251 sends one frame of input image data VIN already stored therein to the subtraction circuit 252 while storing a new one frame of input image data VIN inputted to the motion detection circuit 250. That is, the input image data VIN is delayed for one frame by passing through the memory 251.

The subtraction circuit 252 obtains a difference between the input image data VIN newly inputted from the A-D conversion circuit 222 to the motion detection circuit 250 and the input image data VIN of one frame ago outputted from the memory 251. Specifically, the subtraction circuit 252 subtracts intensity data of each pixel constituting the newly inputted input image data VIN from intensity data of a corresponding pixel constituting the input image data VIN of one frame ago, and converts the subtraction results into absolute values to store the absolute values as a difference image. As described above, the subtraction circuit 252 obtains the changing amount of the input image data VIN inputted from the A-D conversion circuit 222 to the motion detection circuit 250. Therefore, as the changing amount of the input image data VIN with respect to the input image data VIN of one frame ago becomes large, the number of pixels having large absolute values in the difference image increases.

The binarization circuit 253 compares the difference obtained by the subtraction circuit 252 for each pixel with the predetermined threshold. When the difference is larger than or equal to the predetermined threshold, the pixel is defined as "1", and when the difference is smaller than the predetermined threshold, the pixel is defined as "0". That is, the binarization circuit 253 classifies the pixels into pixels having larger changing amounts (i.e., large-moving pixels) and pixels having smaller changing amounts (i.e., small-moving pixels). The binarization circuit 253 executes the binarization for all the pixels constituting the input image data VIN, and records the results as a binarized image.

The histogram circuit 254 obtains a histogram for the binarized image obtained by the binarization circuit 253. Specifically, the histogram circuit 254 scans data of all the pixels constituting the binarized image, and counts the pixels whose data is "1". As described above, a pixel having data of "1" in the binarized image means a pixel having a large changing amount (i.e., a large-moving pixel). Therefore, the count of pixels having data of "1" represents the changing amount of the input image data VIN. Then, the count of pixels having data of "1" obtained by the histogram circuit 254 is transmitted to the frame memory 223 as the moving amount MD of each input image data VIN.

As described above, the motion detection circuit 250 accommodated in the processor 200 for the electronic endoscope according to the embodiment obtains the moving amount MD of the input image data VIN inputted to the motion detection circuit 250 from the A-D conversion circuit 222, and the input image data VIN and the moving amount MD are sequentially stored in the first memory 223a and the second memory 223b of the frame memory 223. Then, through an image record/reproduction operation which is described later, the input image data VIN and the moving amount MD stored in the first memory 223a and the second memory 223b are read out, and a still image having a lower level of blur or color drift is automatically obtained. Storing of data into the first memory 223a and the second memory 223b or reading of data from the first memory 223a and the second memory 223b, i.e., the image record/reproduction operation, is executed under control of the timing generator 225 and the CPU 210.

Figure 4:
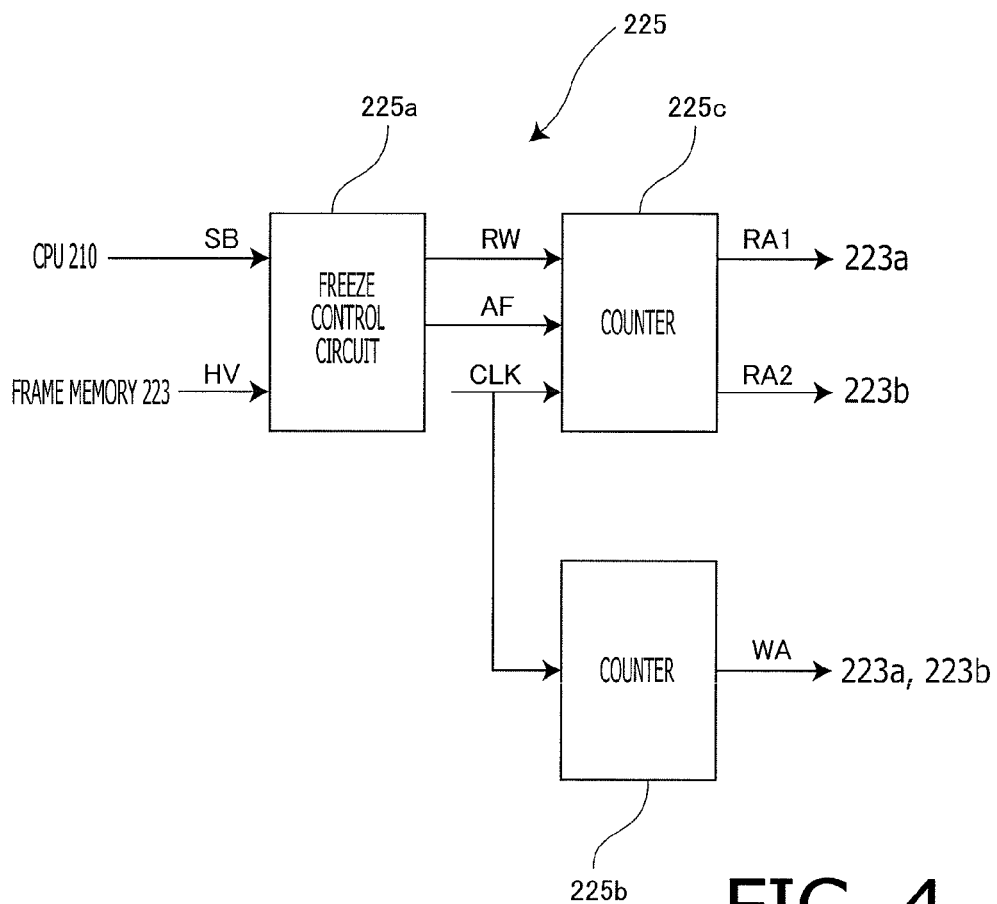
FIG. 4 is a block diagram illustrating a configuration of a timing generator accommodated in the processor for the electronic endoscope according to the first embodiment of the invention.
Figure 5:
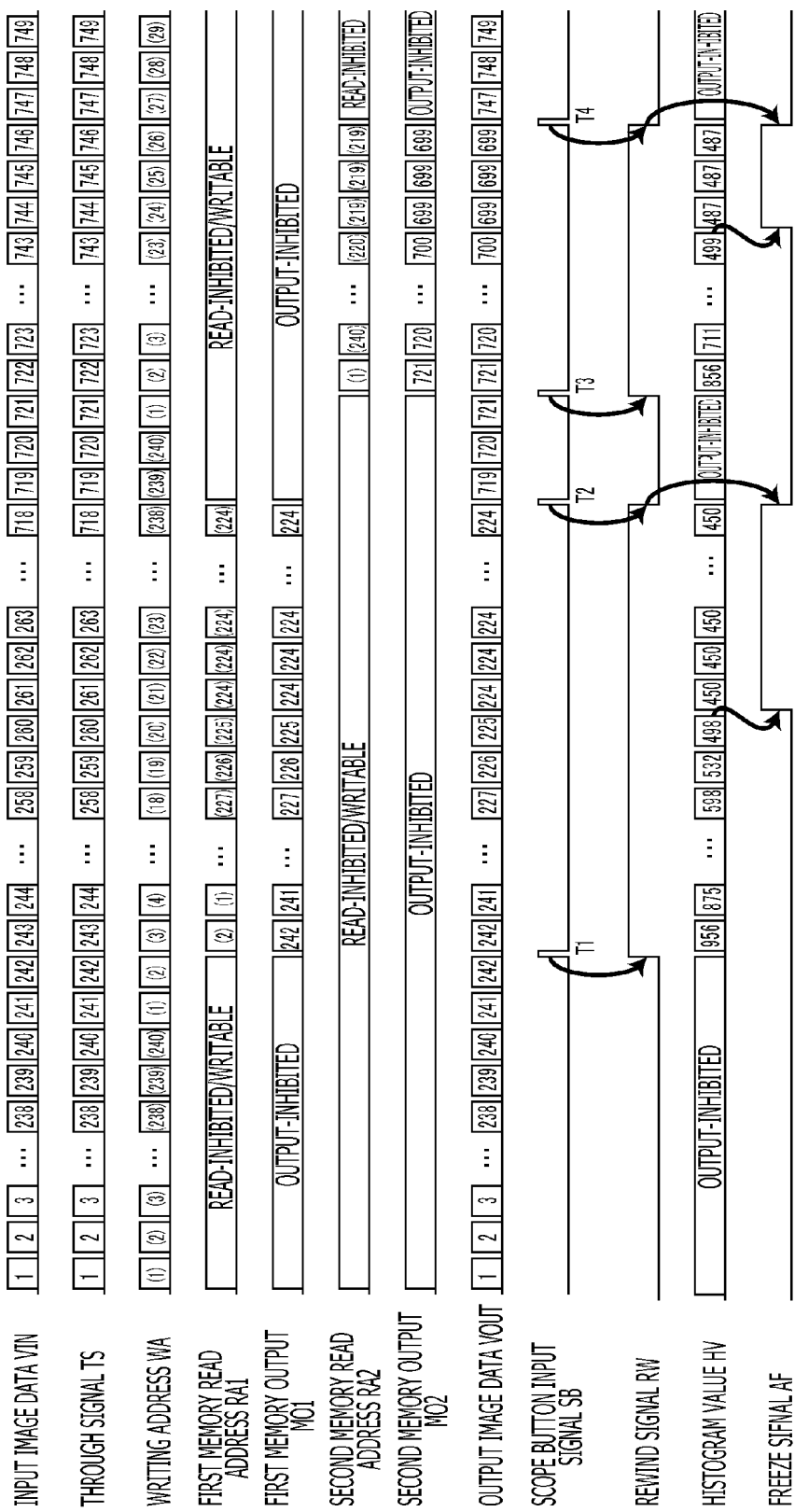
FIG. 5 is a timing chart illustrating an image record/reproduction operation executed on the electronic endoscope apparatus according to the first embodiment of the invention.

Next, the image record/reproduction operation to be executed on the electronic endoscope apparatus 1 according to the embodiment is explained with reference to FIGS. 4 and 5. FIG. 4 is a block diagram illustrating a configuration of the timing generator 225 accommodated in the processor 200 for the electronic endoscope according to the embodiment. FIG. 5 is a timing chart illustrating the image record/reproduction operation executed on the electronic endoscope apparatus 1 according to the embodiment. In FIGS. 4 and 5, to signals common to FIGS. 4 and 5, the same reference numbers are assigned. The same applies to signals common to FIGS. 1 to 3.

As shown in FIG. 4, the timing generator 225 includes a freeze control circuit 225a, a first counter 225b, and a second counter 225c.

The freeze control circuit 225a generates a rewind signal RW and a freeze signal AF based on a scope button input signal SB from the CPU 210 and a histogram value HV outputted from the switch circuit 223c of the frame memory 223. The scope button input signal SB is outputted from the CPU 210 when the CPU 210 detects pressing of the scope button 140 (FIG. 1).

The counter 225b is a counter for generating the writing address WA. The counter 225b generates the writing address WA based on a clock signal CLK inputted from a clock circuit (not shown), and outputs the writing address WA to the first memory 223a and the second memory 223b.

The second counter 225c is a counter for generating the first memory read address RA1 and the second memory read address RA2. The second counter 225c generates the first memory read address RA1 and the second memory read address RA2 based on the clock signal CLK inputted from the clock circuit (not shown), the rewind signal RW and the freeze signal AF inputted from the freeze control circuit 225a, and outputs the first memory read address RA1 and the second memory read address RA2 to the first memory 223a and the second memory 223b, respectively.

As described above, when the electronic endoscope 100, the processor 200 for the electronic endoscope and the monitor 300 are turned on, the image signal outputted from the image pick-up device 120 is sent to the CCD process circuit 221, and is digitized by the A-D conversion circuit 222, and then the input image data VIN is sequentially inputted to the frame memory 223. The CPU 210 of the processor 200 for the electronic endoscope executes a program stored in a memory (not shown), and starts the image record/reproduction process.

FIG. 5 illustrates states of various signals (data) inputted to and outputted from the frame memory 223, the scope button input signal SB, the rewind signal RW and the freeze signal AF. Numbers (without parentheses) assigned to the input image data VIN are used for convenience of explanation, and indicate the frame numbers of the input image data VIN sequentially inputted to the frame memory 223. In addition, numbers (without parentheses) assigned to the through signal TS, the first memory output MO1, the second memory output MO2 and the output image data VOUT indicate the relationship between these signals and the input image data VIN. For example, output "238" of the output image data VOUT indicates that the input image data VIN inputted to the frame memory 223 as "frame number: 238" is outputted. Furthermore, numbers with parentheses assigned to the writing address WA, the first memory read address RA1 and the second memory read address RA2 indicate addresses to be accessed in the first memory 223a and the second memory 223b. As described above, each of the first memory output MO1 and the second memory output MO2 is data constituted by the image data and the moving amount MD; however, only the respective image data (the frame numbers of the input image data VIN) are illustrated for convenience of explanation.

As shown in FIG. 5, in the state where the first memory 223a and the second memory 223b are set to the writable state (the read-inhibited state) (i.e., until the time T1 when the scope button input signal SB is inputted), when the input image data VIN is inputted to the frame memory 223 and the motion detection circuit 250, the input image data VIN and the moving amount MD are stored in the first memory 223a and the second memory 223b at addresses indicated by the writing address WA (FIG. 2). Then, the writing address WA is incremented each time the input image data VIN is stored under control of the timing generator 225. Therefore, in this state, the input image data VIN and the moving amount MD successively inputted to the frame memory 223 and the motion detection circuit 250 are stored in the first memory 223a and the second memory 223b at addresses indicated by the writing address WA. Since, as described above, each of the first memory 223a and the second memory 223b is constituted by a ring-type memory capable of storing 240 frames of image data, after the image data of the 240-th frame and the moving amount MD thereof are stored, the writing address WA is set to "1", and a memory area in which the image data of the first frame is stored is overwritten with the image data of the 241-th frame. As described above, during a time period to the time when the scope button 140 is pressed (a time period to the time T1 when the scope button input signal SB is inputted), 240 frames of the image data and the moving amount MD thereof are sequentially stored in the first memory 223a and the second memory 223b in an updating manner. The switch circuit 223c is configured to select and output the through signal TS until the scope button 140 is pressed, under control of the timing generator 225. Therefore, the same data as the input image data VIN is outputted as the output image data VOUT. The state where the input image data VIN and the moving amount MD thereof are sequentially stored in the first memory 223a and the second memory 223b and the through signal TS is outputted as the output image data VOUT as described above is referred to as a first mode. It should be noted that while the switch circuit 223c selects the through signal TS, output of the histogram value HV is inhibited.

When the CPU 210 detects pressing of the scope button 140 in the first mode, the CPU 210 outputs the scope button input signal SB to the timing generator 225 (T1). Then, the timing generator 225 which has received the scope button input signal SB sets the rewind signal to "High" to execute a first rewind reproduction process. When the first rewind reproduction process is executed, the timing generator 225 sets the first memory 223*a* in a writing-inhibited state (a readable state), and switches the output of the switch circuit 223*c* to the first memory output MO1. The second counter 225*c* sets the first memory read address RA1 to the immediately previous value of the wiring address WA. Then, each time the new input image data VIN is inputted to the frame memory 223, the second counter 225*c* decrements the first memory read address RA1. In the case of FIG. 5, when the scope button 140 is pressed (T1), the immediately previous wiring address WA is "2", and the data stored at the address is the input image data VIN of the "frame number: 242". Therefore, when the scope button 140 is pressed, initially, "2" is set at the first memory read address RA1, and the input image data VIN of the "frame number: 242" is read out. Then, each time the new input image data VIN is inputted to the frame memory 223, the first memory read address RA1 is decremented as "1", "240", "239" . . . , and the input image data VIN of the frames "frame number: 241", "frame number: 240", "frame number: 239" are sequentially outputted.

In concurrent with execution of the first rewind reproduction process and reading out of the input image data VIN stored in the first memory 223*a*, the histogram value HV representing the moving amount MD of the read out input image data VIN is inputted to the freeze control circuit 225*a* of the timing generator 225 from the frame memory 223. In the case of FIG. 5, when the input image data VIN of "frame number: 242", "frame number: 241" . . . is sequentially read out, the histogram value HV of "956", "875" . . . corresponding to the input image data VIN is inputted to the freeze control circuit 225*a* of the timing generator 225 from the frame memory 223.

The freeze control circuit 225*a* monitors the histogram value HV inputted from the frame memory 223 and compares the histogram value HV with the predetermined threshold. When the histogram value HV becomes smaller than or equal to the predetermined threshold, the freeze signal AF is set to "High". As a result, the second counter 225*c* stops to decrement the first memory read address RA1. In this embodiment, the freeze control circuit 225*a* detects whether the histogram value HV becomes smaller than or equal to the predetermined threshold of "500", and, in the case of FIG. 5, the freeze control circuit 225*a* detects that the histogram value HV becomes smaller than or equal to the predetermined threshold "500" when the histogram value of "498" is detected, and sets the freeze signal AF to "High". As a result, decrement for the first memory read address RA1 is stopped, and the address "224" is maintained. Then, the input image data VIN of "frame number: 224" stored at the address "224" in the first memory 223*a* is read and outputted. Consequently, the input image data VIN of the "frame number: 224" is displayed on the monitor 300 as a still image. As described above, since the histogram value HV is data representing the moving amount MD of the input image data VIN, the input image data VIN of the "frame number: 224" repeatedly displayed on the monitor 300 is an image having a small moving amount MD (i.e., an image having a lower level of blur or color drift).

As described above, when the first rewind reproduction process is executed, the image data stored in the first memory 223*a* is read out in reverse chronological order from the latest frame, and as a result the video is outputted in a rewinding manner. When the histogram value HV becomes smaller than or equal to the predetermined threshold, and thereby it is judged that the image has a lower level of blur or color drift, a still image is obtained automatically. The second memory 223*b* is still in the read-inhibited state (the writable state) even when the first rewind reproduction process is executed, and the input image data VIN and the moving amount MD are sequentially stored in the second memory 223*b* at the address indicated by the writing address WA. As described above, the state where the image data and the moving amount MD are read from the first memory 223*a* and outputted while storing the input image data VIN and the moving amount MD in the second memory 223*b* is referred to as a second mode.

When the CPU 210 detects pressing of the scope button 140 in the second mode, the CPU 210 outputs the scope button input signal SB to the timing generator 225 (T2). Then, the timing generator 225 which has received the scope button input signal SB sets the rewind signal RW and the freeze signal AF to "Low", and thereby the first rewind reproduction process is stopped. When the first rewind reproduction process is stopped, the timing generator 225 sets the first memory to the read-inhibited state (the writable state) and switches the output of the switch circuit 223*c* to the through signal TS, under control of the CPU 210. As a result, the input image data VIN and the moving amount MD are sequentially stored in the first memory 223*a* again, and the same data as the input image data VIN is outputted as the output image data VOUT. That is, the mode returns to the first mode.

When the CPU 210 detects that the scope button 140 is pressed, the CPU 210 outputs the scope button input signal SB to the timing generator 225 (T3). Then, the timing generator 225 which has received the scope button input signal SB sets the rewind signal to "High", and thereby a second rewind reproduction process is executed. When the second rewind reproduction process is executed, the timing generator 225 sets the second memory 223*b* to the writing-inhibited state (the readable state), and switches the output of the switch circuit 223*c* to the second memory output MO2. The second counter 225*c* sets the second memory read address RA2 to the immediately previous value of the writing address WA. Then, each time the new input image data VIN is inputted to the frame memory 223, the second counter 225*c* decrements the second memory read address RA2. In the case of FIG. 5, when the scope button 140 is pressed (T3), the immediately previous writing address WA is "1", and the data stored at the address is the input image data VIN of the "frame number: 721". Therefore, when the scope button 140 is pressed, initially "1" is set to the second memory read address RA2, and the input image data VIN of the "frame number: 721" is read out. Then, each time the new input image data VIN is inputted to the frame memory 223, the second memory read address RA2 is decremented as "240", "239", "238" . . . , and the input image data VIN of the "frame number: 720", "frame number: 719", "frame number: 718" . . . is sequentially read out and outputted.

In concurrent with execution of the second rewind reproduction process and reading out of the input image data VIN stored in the second memory 223*b*, the histogram value HV representing the moving amount MD of the read out input image data VIN is inputted to the freeze control circuit 225*a* of the timing generator 225 from the frame memory 223. In the case of FIG. 5, when the input image data VIN of "frame number: 721", "frame number: 720" . . . is sequentially read out, the histogram value HV of "856", "711" . . . corresponding to the input image data VIN is sequentially inputted to the freeze control circuit 225*a* of the timing generator 225 from the frame memory 223.

The freeze control circuit 225*a* monitors the histogram value HV inputted from the frame memory 223, and compares the histogram value HV with the predetermined threshold. When the histogram value HV becomes smaller than or equal to the predetermined threshold, the freeze signal AF is set to "High". As a result, the second counter 225c stops to decrement the second memory read address RA2. In this embodiment, the freeze control circuit 225a detects whether the histogram value HV becomes smaller than or equal to the predetermined threshold of "500". In the case of FIG. 5, when the histogram value HV of "499" is detected, it is judged that the histogram value HV becomes smaller than or equal to "500", and the freeze signal AF is set to "High". Consequently, decrement of the second memory read address RA2 is stopped, and the address "219" is maintained. Then, the input image data VIN of the "frame number: 699" stored at the address "219" in the second memory 223b is read out repeatedly. Thus, the input image data VIN at the "frame number: 699" is displayed on the monitor 300 as a still image. As in the case of the first rewind reproduction process, the histogram value HV is data representing the moving amount MD of the input image data VIN. Therefore, the input image data VIN of the "frame number: 699" repeatedly displayed on the monitor 300 is an image having a small moving amount MD (i.e., an image having a lower level of blur or color drift).

As described above, when the second rewind reproduction process is executed, the image data stored in the second memory 223b is sequentially outputted in reverse chronological order from the latest frame, and the video is outputted in a rewinding manner. When the histogram value HV becomes smaller than or equal to the predetermined threshold and thereby it is judged that the image has a lower level of blur and color drift, a still image is obtained automatically. The first memory 223a is still in the read-inhibited state (the writable state) even when the second rewind reproduction process is executed, and the input image data VIN and the moving amount MD are sequentially stored at the address indicated by the writing address WA. As described above, the state where the image data and the moving amount MD are read out from the second memory 223b while storing the input image data VIN and the moving amount MD in the first memory 223a is referred to as a third mode.

In the third mode, when the CPU 210 detects that the scope button 140 is pressed, the CPU 210 outputs the scope button input signal SB to the timing generator 225 (T4). Then, the timing generator 225 which has received the scope button input signal SB sets the rewind signal RW and the freeze signal AF to "Low", and thereby the second rewind reproduction process is stopped. When the second rewind reproduction process is stopped, the timing generator 225 sets the second memory 223b as the read-inhibited state (the writable state), and switches the output of the switch circuit 223c to the through signal TS, under control of the CPU 210. As a result, the input image data VIN and the moving amount MD are sequentially stored in the second memory 223b again, and the same data as the input image data VIN is outputted as the output image data VOUT. That is, the mode returns to the first mode. It should be noted that, when pressing of the scope button 140 is detected thereafter, the above described mode transition is caused, i.e., each time pressing of the scope button 140 is detected, the mode changes in order of the second mode, the first mode, the third mode, the first mode.

As described above, in the electronic endoscope apparatus 1 according to the embodiment, each time pressing of the scope button 140 is detected by the CPU 210, the mode changes in order of the first mode, the second mode, the first mode, the third mode and the first mode. In the second mode, the image data and the moving amount MD are read from the first memory 223a while storing the input image data VIN and the moving amount MD in the second memory 223b. In the third mode, the image data and the moving amount MD are read out from the second memory 223b while storing the input image data VIN and the moving amount MD in the first memory 223a. That is, even when one of the first memory 223a and the second memory 223b is set as the readable state for the image data and the moving amount MD (i.e., the writing-inhibited state), the other continues to sequentially store the input image data VIN and the moving amount MD. Therefore, even when the first rewind reproduction process or the second rewind reproduction process is running, 240 frames of image data and the moving amounts MD thereof are stored in one of the first memory 223a and the second memory 223b. In addition, as described above, a still image is automatically obtained in the second mode or the third mode. Therefore, in the case where a desired still image is not obtained by one operation, i.e., in the case where a desired still image is not obtained in the second mode, a still image can be re-shot in the third mode without waiting for accumulation of the new image data in a memory even if an operation for obtaining a still image is repeated soon.

(Variation of First Embodiment)

In the first embodiment, the image data and the moving amount MD stored in the first memory 223a and the second memory 223b are read out in reverse chronological order from the latest frame in the first rewind reproduction process (the second mode) and the second rewind reproduction process (the third mode). However, the present invention is not limited to such a configuration. For example, the image data and the moving amount MD stored in the first memory 223a and the second memory 223b may be thinned out, and the data may be read out in reverse chronological order from the latest frame at intervals of a few frames. With this configuration, a still image having a small moving amount MD (i.e., having a lower level of blur or color drift) can be obtained at a high speed. Furthermore, the thinned out image data is sequentially displayed on the monitor 300 until a still image is obtained, an operator does not lose track of a diseased portion being watched.

In the first embodiment, each time pressing of the scope button 140 is detected by the CPU 210, the mode is changed from the first mode in order of the second mode, the first mode, the third mode, the first mode. However, the present invention is not limited to such a configuration. For example, in the case where the mode is changed from the second mode to the first mode, the mode may be changed to the third mode when pressing of the scope button 140 is detected within a predetermined time period from the transition, and the mode may be changed to the second mode again when pressing of the scope button 140 is detected after the predetermined time has elapsed from the transition. Each of the first memory 223a and the second memory 223b according to the first embodiment is configured to be able to store 240 frames of image data. Therefore, when the frame rate of the image signal outputted from the image pick-up device 120 is 60 frames/sec, the image data corresponding to immediately previous 4 seconds is stored in the first memory 223a and the second memory 223b, respectively. In other words, the image data in the first memory 223a and the second memory 223b is completely replaced (refreshed) at every four seconds. Therefore, when the mode is changed from the second mode to the first mode, the mode may move again to the second mode after the time period (four seconds) required for refresh of the first memory 223a has elapsed after the transition.

(Second Embodiment)

Figure 6:
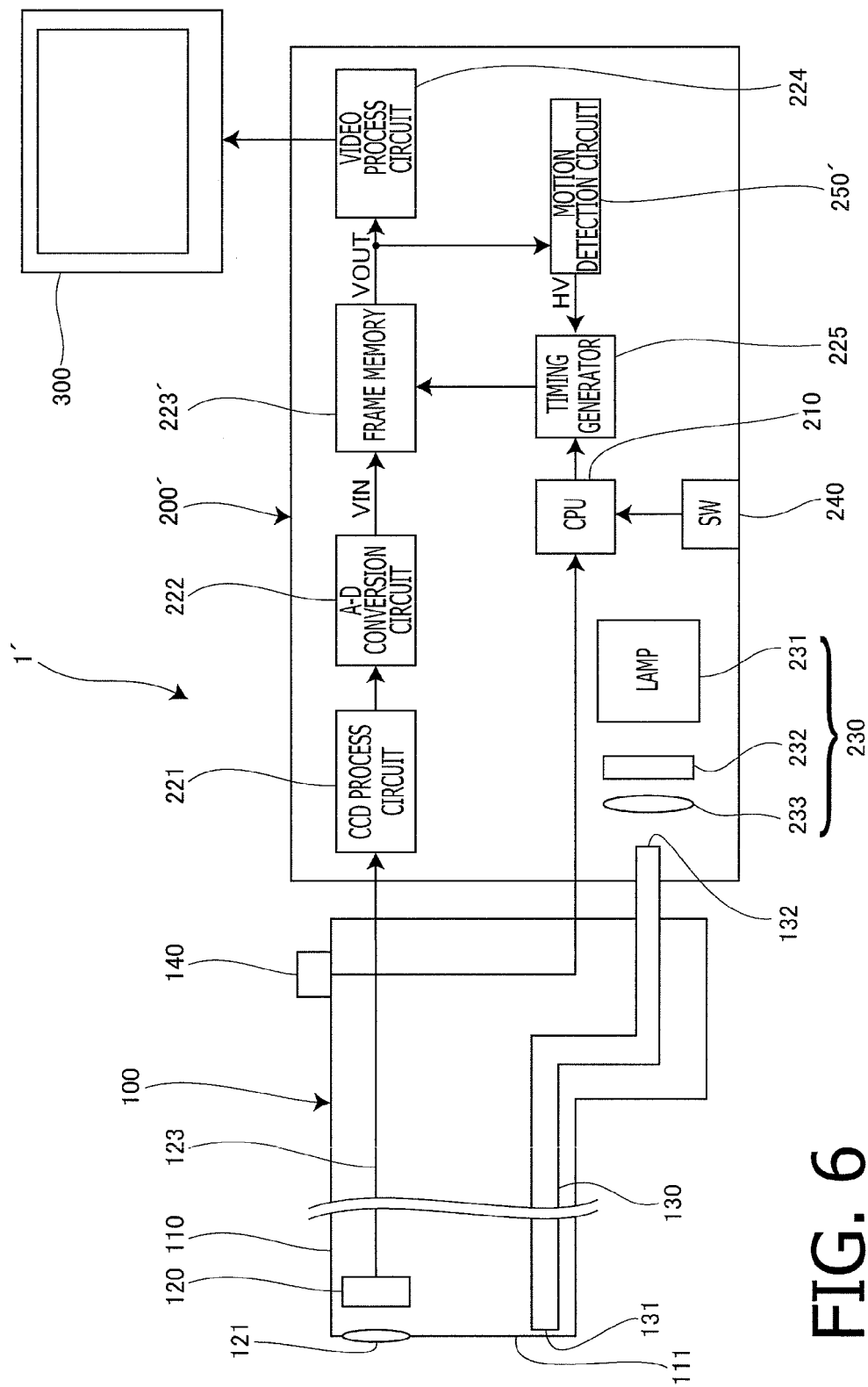
FIG. 6 is a block diagram of an electronic endoscope apparatus according to a second embodiment of the invention.
Figure 7:
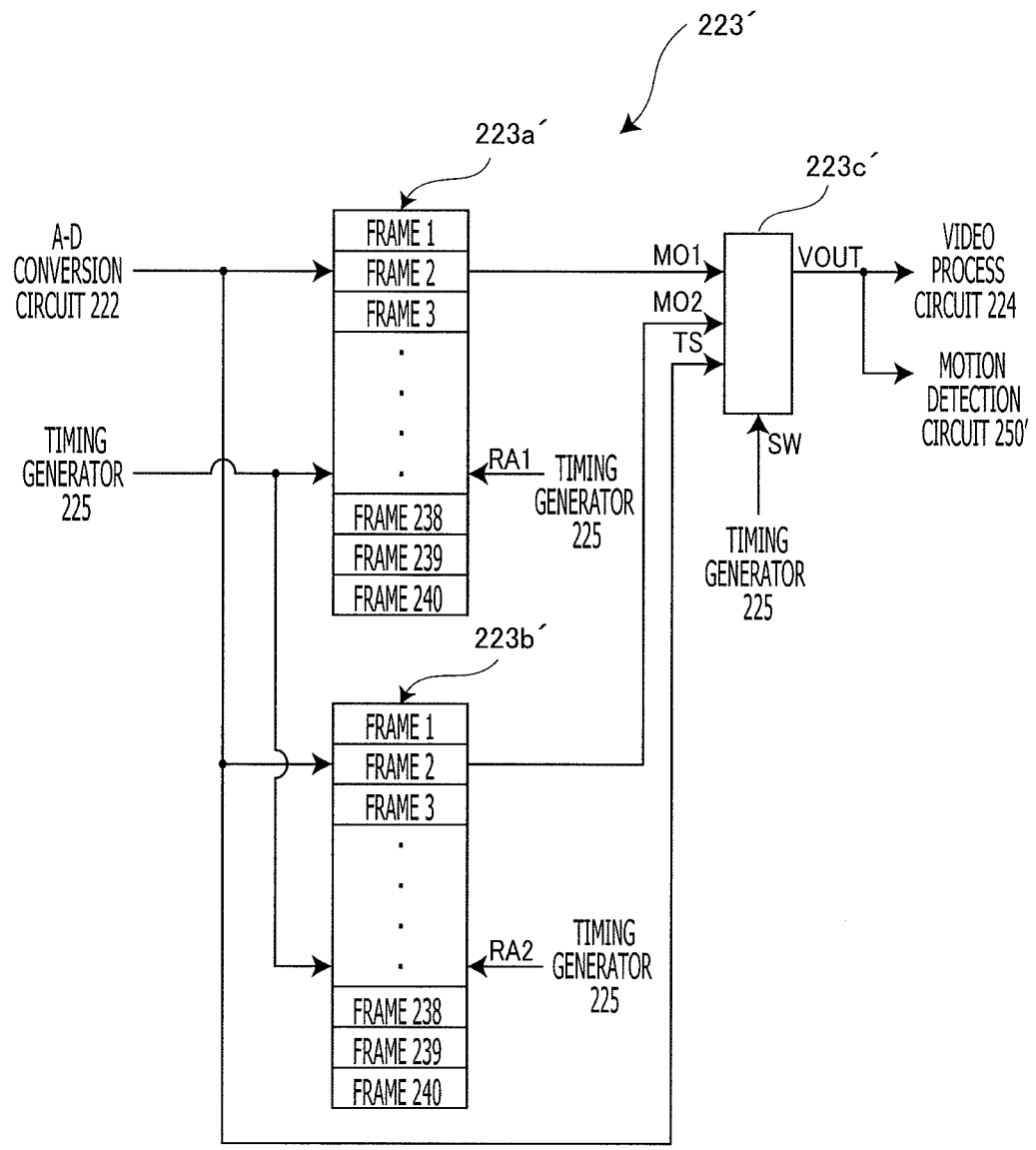
FIG. 7 is a block diagram illustrating a configuration of a frame memory accommodated in a processor for an electronic endoscope according to the second embodiment of the invention.
Figure 8:
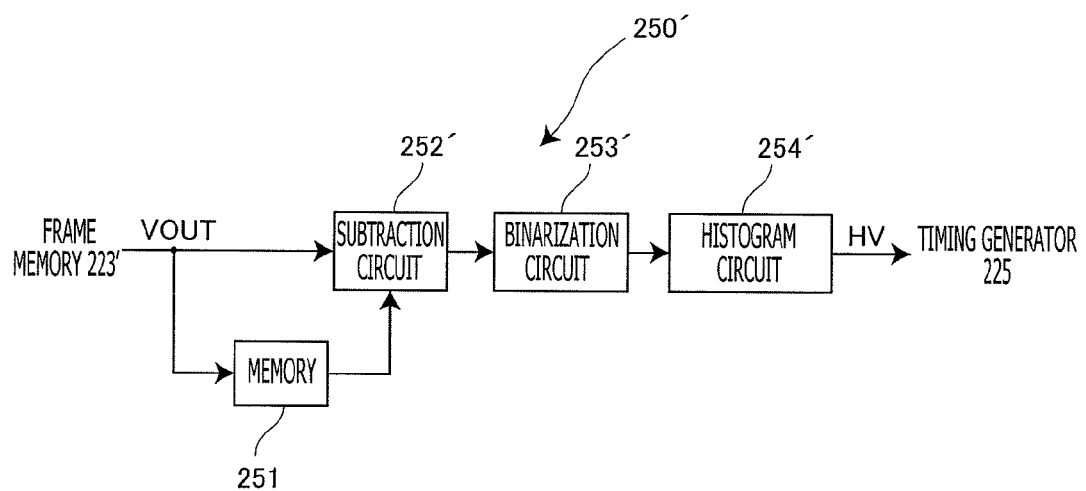
FIG. 8 is a block diagram illustrating a configuration of a motion detection circuit accommodated in the processor for the electronic endoscope according to the second embodiment of the invention.

Hereafter, an electronic endoscope apparatus 1' according to a second embodiment of the invention is explained with reference to FIGS. 6 to 8. FIG. 6 is a block diagram of the electronic endoscope apparatus 1' according to the second embodiment of the invention. FIG. 7 is a block diagram illustrating a configuration of a frame memory 223' accommodated in a processor 200' for an electronic endoscope according to the second embodiment of the invention. FIG. 8 is a block diagram illustrating a configuration of a motion detection circuit 250' accommodated in the processor 200' for the electronic endoscope according to the second embodiment of the invention.

The electronic endoscope apparatus 1' according to the second embodiment of the invention is different from the electronic endoscope apparatus 1 according to the first embodiment shown in FIGS. 1 to 4 in regard to the configuration of the frame memory 223' and the motion detection circuit 250'. In the following, explanation is given in detail for the difference from the first embodiment. In FIGS. 6 to 8, to elements which are common to the first embodiment, same reference numbers are assigned.

As shown in FIG. 6, to the motion detection circuit 250' of the electronic endoscope apparatus 1' according to the second embodiment, the output image data VOUT of the frame memory 223' is inputted, and the motion detection circuit 250' outputs the histogram value HV to the timing generator 225.

As shown in FIG. 7, as in the case of the first embodiment, the frame memory 223' according to the second embodiment includes a first memory 223a', a second memory 223b' and a switch circuit 223c'. Each of the first memory 223a' and the second memory 223b' is a ring-type memory constituted, for example, by a DRAM. To the first memory 223a' and the second memory 223b', digital image data outputted from the A-D conversion circuit 222 is inputted sequentially, and is stored sequentially at predetermined addresses, such as frame 1, frame 2 . . . . The frame memory 223' according to the second embodiment is different from the first embodiment in that no data is inputted from the motion detection circuit 250' to the frame memory 223' and the moving amount MD is not stored in the first memory 223a' and the second memory 223b'. The first memory 223a' and the second memory 223b' are connected to the timing generator 225, the writing address WA and the first memory read address RA1 are inputted to the first memory 223a', and the writing address WA and the second memory read address RA2 are inputted to the second memory 223b'. Since the writing operation (storing operation) and the reading operation with respect to the first memory 223a' and the second memory 223b' are the same as those of the first embodiment, explanations thereof are omitted.

The switch circuit 223c' is a circuit for switching the input signal, and is constituted, for example, by a multiplexer. The first memory output MO 1, the second memory output MO2 and the through image signal TS (i.e., the input image data VIN) are inputted to the switch circuit 223c', and, under control of the timing generator 225, one of the first memory output MO1, the second memory output MO2 and the through image signal TS is selected and is outputted as the output image data VOUT. That is, the second embodiment is different from the switch circuit 223c of the first embodiment in that the moving amount MD is not contained in the first memory output MO1 and the second memory output MO2 and therefore there is no necessity to separate the moving amount MD. In addition, the second embodiment is different from the first embodiment in that the output image data VOUT outputted from the switch circuit 223c' is sent to the video process circuit 224 and the motion detection circuit 250'.

As shown in FIG. 8, the motion detection circuit 250' according to the second embodiment includes a memory 251' which records a frame of output image data VOUT inputted from the frame memory 223', a subtraction circuit 252' which obtains a difference between the output image data VOUT inputted to the motion detection circuit 250' and the output image data VOUT stored in the memory 251' one frame ago, a binarization circuit 253' which binarizes the difference obtained by the subtraction circuit 252' by comparing the difference with a predetermined threshold, and a histogram circuit 254' which obtains a histogram for a binarization result by the binarization circuit 253'.

The output image data VOUT inputted to the motion detection circuit 250' is transmitted to the memory 251' and the subtraction circuit 252'. The memory 251' sends the one frame of output image data VOUT already stored therein to the subtraction circuit 252' while storing a new one frame of output image data VOUT inputted to the motion detection circuit 250'. That is, the output image data VOUT is delayed for one frame by passing through the memory 251'.

The subtraction circuit 252' obtains a difference between the output image data VOUT newly inputted to the motion detection circuit 250' and the output image data VOUT of one frame ago outputted from the memory 251'. Specifically, the subtraction circuit 252' subtracts intensity data of each pixel constituting the newly inputted output image data VOUT from intensity data of a corresponding pixel constituting the output image data VOUT of one frame ago, and converts the subtraction results into absolute values to store the absolute values as a difference image. As described above, the subtraction circuit 252' obtains the changing amount of the output image data VOUT inputted to the motion detection circuit 250' from the frame memory 223'. Therefore, as the changing amount of the output image data VOUT with respect to the output image data VOUT of one frame ago becomes large (i.e., as the moving amount becomes large), the number of pixels having large absolute values in the difference image increases.

The binarization circuit 253' compares the difference obtained by the subtraction circuit 252' for each pixel with the predetermined threshold. When the difference is larger than equal to the predetermined threshold, the pixel is defined as "1", and when the difference is smaller than the predetermined threshold, the pixel is defined as "0". That is, the binarization circuit 253' classifies the pixels into pixels having larger changing amounts (i.e., large-moving pixels) and pixels having smaller changing amounts (i.e., small-moving pixels). The binarization circuit 253' executes binarization for all the pixels constituting the output image data VOUT, and records the results as a binarized image.

The histogram circuit 254' obtains a histogram for the binarized image obtained by the binarization circuit 253'. Specifically, the histogram circuit 254' scans data of all the pixels constituting the binarized image, and counts the pixels whose data are "1". As described above, a pixel having data of "1" in the binarized image means a pixel having large changing amount (i.e., a large-moving pixel). Therefore, the count of pixels having data of "1" represents the changing amount of the output image data VOUT. Then, the count of pixels having data of "1" obtained by the histogram circuit 254' is transmitted to the timing generator 225 as the moving amount MD of each output image data VOUT.

As described above, the motion detection circuit 250' accommodated in the electronic endoscope apparatus 1' according to the second embodiment sequentially obtains, as the histogram value HV, the moving amount MD of the output image data VOUT inputted from the frame memory 223', and transmits the histogram value HV to the timing generator 225. Then, as in the case of the first embodiment, through the image record/reproduction operation under control of the timing generator 225 and the CPU 210, the input image data VIN stored in the first memory 223a' and the second memory 223b' is read out and the moving amount MD (the histogram value HV) is obtained, and thereby a still image having a lower level of blur or color drift is automatically obtained. According to the second embodiment, there is no necessity to store the moving amount MD of the input image data VIN in the first memory 223a' and the second memory 223b'. Therefore, in contrast to the first embodiment, it is possible to use a smaller capacity memory as the first memory 223a' and the second memory 223b'.

As described above, in the first and second embodiments of the invention, switching between the first mode to the third mode of the image record/reproduction operation is performed based on an operation with respect to the scope button 140 of the electronic endoscope 100; however, the present invention is not limited to such a configuration. For example, switching between the first mode and to the third mode may be performed based on an operation with respect to the switch 240 of the processor 200 for the electronic endoscope.

What is claimed is:

1. A processor for an electronic endoscope for processing an image signal from the electronic endoscope and displaying an image on a monitor, comprising:
    an image data generator that generates a plurality of frames of image data from the image signal;
    first and second image storages, each of which stores the plurality of frames of image data;
    a motion detector that obtains a difference for each frame of the plurality of frames of image data by comparing the frame of image data with an immediately preceding frame of plurality of frames of image data;
    a signal processor that converts the plurality of frames of image data into a video signal which is displayed on the monitor; and
    a controller that controls the signal processor and the first and second image storages,
    wherein the controller performs control according to one of:
    a first mode, in which the plurality of frames of image data generated by the image data generator are sequentially converted into the video signal and are outputted, and the plurality of frames of image data and the difference are sequentially stored in the first and second image storages;
    a second mode, in which the plurality of frames of image data stored in the first image storage are converted into the video signal and are outputted, and the plurality of frames of image data generated by the image data generator and the difference are sequentially stored in the second image storage; and
    a third mode, in which the plurality of frames of image data stored in the second image storage are converted into the video signal and are outputted, and the plurality of frames of image data generated by the image data generator and the difference are sequentially stored in the first image storage,
    wherein in the second and third modes, the difference is monitored, and, based on the difference, a first reproduction mode is switched into a second reproduction mode, wherein, in the first reproduction mode, the plurality of frames of image data stored in the first image storage or the second image storage are successively converted into the video signal in a reverse chronological order in regard to stored times, and in the second reproduction mode, one of the plurality of frames of image data stored in the first and second image storages is repeatedly converted into the video signal and is outputted,
    wherein the processor further comprises a judger that receives an input of a control signal for switching from the first mode to the second or the third mode and for switching from the third mode or second mode to the first mode, and makes a judgment on which of the second mode and the third mode the controller switches to, when the control signal is inputted in the first mode,
    wherein the controller switches from the second mode to the first mode, when the control signal is inputted in the second mode,
    wherein, in response to the controller switching from the second mode to the first mode, the judger makes a judgment to switch from the first mode to the third mode only when the control signal is inputted within a predetermined time from a time when the controller switches from the second mode to the first mode, and
    wherein the predetermined time is determined based on a maximum number of frames of image data which can be stored in the first image storage.

2. The processor for an electronic endoscope according to claim 1,
    wherein the controller compares the difference with a predetermined threshold, and when the difference becomes smaller than or equal to the predetermined threshold, the controller switches from the first reproduction mode to the second reproduction mode.

3. The processor for an electronic endoscope according to claim 1,
    wherein, in the first reproduction mode of the second mode, the plurality of frames of image data stored in the first image storage are converted into the video signal at intervals of a few frames and are outputted, and
    in the first reproduction mode of the third mode, the plurality of frames of image data stored in the second image storage are converted into the video signal at intervals of a few frames and are outputted.

4. The processor for an electronic endoscope according to claim 1,
    wherein the judger makes a judgment such that the second mode and the third mode are alternately switched each time the control signal is inputted.

5. A processor for an electronic endoscope for processing an image signal from the electronic endoscope and displaying an image on a monitor, comprising:
    an image data generator that generates image data from the image signal;
    first and second image storages, each of which stores a plurality of frames of image data;
    a motion detector that, when the image data stored in the first and second image storages is outputted, obtains a difference by comparing each frame of the output image data with an immediately preceding frame of the output image data;
    a signal processor that converts the image data into a video signal which is displayed on the monitor; and
    a controller that controls the signal processor and the first and second image storages,
    wherein the controller performs control according to one of:
    a first mode, in which the image data generated by the image data generator is sequentially converted into the video signal and is outputted, and the image data is sequentially stored in the first and second image storages;

a second mode, in which the image data stored in the first image storage is converted into the video signal and is outputted, and the image data generated by the image data generator is sequentially stored in the second image storage; and a third mode, in which the image data stored in the second image storage is converted into the video signal and is outputted, and the image data generated by the image data generator is sequentially stored in the first image storage, wherein, in the second and third modes, the difference is monitored, and, based on the difference, a first reproduction mode is switched into a second reproduction mode, wherein, in the first reproduction mode, the plurality of frames of image data stored in the first image storage or the second image storage are successively converted into the video signal in a reverse chronological order in regard to stored times, and in the second reproduction mode, one of the plurality of frames of image data stored in the first and second image storages is repeatedly converted into the video signal and is outputted, wherein the processor further comprises a judger that receives an input of a control signal for switching from the first mode to the second mode or the third mode and for switching from the third mode or second mode to the first mode, and makes a judgment on which of the second mode and the third mode the controller switches to, when the control signal is inputted in the first mode, wherein the controller switches from the second mode to the first mode, when the control signal is inputted in the second mode, wherein, in response to the controller switching from the second mode to the first mode, the judger makes a judgment to switch from the first mode to the third mode only when the control signal is inputted within a predetermined time from a time when the controller switches from the second mode to the first mode, and wherein the predetermined time is determined based on a maximum number of frames of image data which can be stored in the first image storage.

6. The processor for an electronic endoscope according to claim 5,
wherein the controller compares the difference with a predetermined threshold, and when the difference becomes smaller than or equal to the predetermined threshold, the controller switches from the first reproduction mode to the second reproduction mode.

7. The processor for an electronic endoscope according to claim 5,
wherein, in the first reproduction mode, the plurality of frames of image data stored in the first and second image storages are converted into the video signal at intervals of a few frames and are outputted.

8. The processor for an electronic endoscope according to claim 5,
wherein the judger makes a judgment such that the second mode and the third mode are alternately switched each time the control signal is inputted.

9. An electronic endoscope apparatus, comprising:
a processor for an electronic endoscope according to claim 1; and
an electronic endoscope connected to the processor for the electronic endoscope,
wherein the electronic endoscope comprises:
a first inputter that accepts an input for designating switching from the first mode to the second mode or the third mode; and
a second inputter that accepts an input for designating switching from the second and third modes to the first mode.

10. The electronic endoscope apparatus according to claim 9, wherein the first inputter is identical with the second inputter.

11. An electronic endoscope apparatus, comprising:
a processor for an electronic endoscope according to claim 5; and
an electronic endoscope connected to the processor for the electronic endoscope,
wherein the electronic endoscope comprises:
a first inputter that accepts an input for designating switching from the first mode to the second mode or the third mode; and
a second inputter that accepts an input for designating switching from the second and third modes to the first mode.

* * * * *